United States Patent [19]

Takahashi et al.

[11] Patent Number: 4,833,144
[45] Date of Patent: May 23, 1989

[54] 2-ALKYLSULFINYL-4(3H)-QUINAZOLI-NONE DERIVATIVES AND PHARMACEUTICAL COMPOSITIONS

[75] Inventors: Toshihiro Takahashi, Kawagoe; Tatsuo Horaguchi, Fujimi; Koichi Nakamaru, Saitama; Yoshikuni Suzuki, Ohmiya, all of Japan

[73] Assignee: Nisshin Flour Milling Co., Ltd., Japan

[21] Appl. No.: 148,602

[22] Filed: Jan. 26, 1988

[30] Foreign Application Priority Data

Jan. 30, 1987 [JP] Japan .................................. 62-20124
Aug. 20, 1987 [JP] Japan .................................. 62-205072

[51] Int. Cl.$^4$ .................. A61K 31/505; C07D 239/95; C07D 403/12
[52] U.S. Cl. .................................... 514/259; 544/284; 544/285
[58] Field of Search .............. 544/285, 284, 116; 514/259

[56] References Cited

U.S. PATENT DOCUMENTS 4,576,941 3/1986 Suh et al. ........................... 544/285
4,605,657 8/1986 Edwards ............................ 544/285

FOREIGN PATENT DOCUMENTS 225131 7/1985 Fed. Rep. of Germany .

OTHER PUBLICATIONS

Chan, "Chemical Abstracts", vol. 95, 1981, col. 95:6504a.
Benneche et al., "Chemical Abstracts", vol. 97, 1982, col. 97:182352z.
Southon et al., "Chem. Ber.," Band 111 (3), 1978, pp. 1006–1018.
J. Chem. Soc., vol. 82, p. 964 (1960).
J. Med. Chem., vol. 26, 218–222 (1983).
Chem. Abstract, vol. 83, 131542 q (1975).
Chem. Abstract, vol. 92, 146713 F (1980).
Chem. Abstract, vol. 91, 39422t (1979).

Primary Examiner—Glennon H. Hollrah
Assistant Examiner—James H. Turnipseed
Attorney, Agent, or Firm—Abelman Frayne Rezac & Schwab

[57] ABSTRACT

2-Alkylsulfinyl-4(3H)-quinazolinone derivatives of formula (I) are provided.

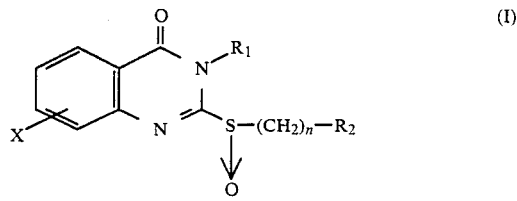

wherein $R_1$ is a $C_1$–$C_6$ alkyl group, an aryl group, a substituted aryl group or an aralkyl group, $R_2$ is a phenyl group, a substituted phenyl group or a 5- or 6-membered heterocyclic group containing one or more N, O or S as a hetero atom or atoms, said heterocyclic group optionally being substituted or fused with a benzene ring, n is 1 or 2 and X is hydrogen, a $C_1$–$C_6$ alkyl group or a halogen atom, and pharmaceutically acceptable acid addition salts thereof. They are useful as anti-ulcer agents.

8 Claims, No Drawings

2-ALKYLSULFINYL-4(3H)-QUINAZOLINONE DERIVATIVES AND PHARMACEUTICAL COMPOSITIONS

FIELD OF THE INVENTION

The present invention relates to new 2-alkylsulfinyl-4(3H)-quinazolinone derivatives, processes for their preparation and their use as antiulcer agents.

BACKGROUND OF THE INVENTION

The agents used as the antiulcer drugs include $H_2$-receptor antagonists, anticholinergic agents, gastric mucosal protective agents and antacids, which are used depending upon the symptom of patients. These known agents, however, are of such drawbacks as generally weak activity and frequent occurrence of side effects.

For example, cimetidine, which is a $H_2$-receptor antagonist widely employed, is known to have side effects such as gynecomatism. Moreover, numbers of cases are reported about recurrence of ulcer after suspension of administration with cimetidine. Anticholinergic agents are known to have such side effects as suppression of gastric motility, corediastasis and thirst. Furthermore, they exhibit activity only for a limited period of time. Antacids are known to have frequent occurrence of such side effects as constipation.

As described above, known antiulcer agents were limitedly used in terms of manner of administration due to their side effects, and they have common drawback of exhibiting somewhat weak activity.

The present invention results from efforts to develop new 2-alkylsulfinyl-4(3H)-quinazolinone derivatives with more improved antiulcer effect.

DISCLOSURE OF THE INVENTION

According to the invention, there are provided 2-alkylsulfinyl-4(3H)-quinazolinone derivatives of formula (I)

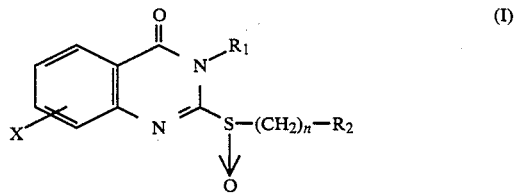

wherein $R_1$ is a $C_1$–$C_6$ alkyl group, an aryl group, a substituted aryl group or an aralkyl group, $R_2$ is a phenyl group, a substituted phenyl group or a 5- or 6-membered heterocyclic group containing one or more N, O or S as a hetero atom or atoms, said heterocyclic group optionally being substituted or fused with a benzene ring, n is 1 or 2 and X is hydrogen, a $C_1$–$C_6$ alkyl group or a halogen atom, and pharmaceutically acceptable acid addition salts thereof.

In the above formula (I), where $R_1$ is a $C_1$–$C_6$ alkyl group, it includes, for example, methyl, ethyl, propyl, isopropyl, butyl, isobutyl or pentyl group.

Where $R_1$ is an aryl group, it is preferably one having from 6 to 10 carbon atoms such as phenyl or naphthyl group.

Where $R_1$ is a substituted aryl group, the aryl group itself may be the same as one previously defined, and the substituent or substituents include, for example, a $C_1$–$C_6$ alkyl group, a $C_1$–$C_6$ alkoxy group and halogen atom.

Where the substituent is a lower alkyl group, it may be the same as that defined for $R_1$.

Where the substituent is a $C_1$–$C_6$ alkoxy group, it includes, for example, methoxy, ethoxy, propoxy, isopropoxy, butoxy, isobutoxy, pentyloxy or hexyloxy group.

Where the substituent is a halogen atom, it includes, for example, fluorine, chlorine, bromine or iodine atom.

Where $R_1$ is an aralkyl group, it is preferably one having from 7 to 99 carbon atoms such as benzyl or phenethyl.

Where $R_2$ is a substituted phenyl group, the substituent or substituents include, for example, a $C_1$–$C_6$ alkylamino group such as di-$C_1$–$C_6$ alkylamino group (e.g. dimethylamino group) or a $C_1$–$C_6$ alkoxy group which may be the same as that defined for the substituent on the aryl group for $R_1$.

Thus, the substituted phenyl group includes, for example, a dimethylaminophenyl or a trimethoxyphenyl group.

Wher $R_2$ is a 5- or 6-membered heterocyclic group containing one or more N, O or S as a hetero atom or atoms, said heterocyclic group optionally being substituted or fused with a benzene ring, the heterocyclic group itself may be, for example, furyl, thienyl, pyridyl (e.g. 2-, 3- or 4-pyridyl) or quinolyl. The substituent or substituents on the heterocyclic group include, for example, a $C_1$–$C_6$ alkyl group or a $C_1$–$C_6$ alkoxy group as exemplified above.

Where X is a $C_1$–$C_6$ alkyl group, it may be the same as that defined for $R_1$.

Where X is a halogen atom, it may likewise be the same as that defined for the substituent on the aryl group of $R_1$.

Concrete examples of the compounds of formula (I) are recited below.

3-phenyl-2-(2-pyridylmethylsulfinyl)-4(3H)-quinazolinone, 3-ethyl-2-(2-pyridylmethylsulfinyl)-4(3H)-quinazolinone, 2-(benzylsulfinyl)-3-phenyl-4(3H)-quinazolinone, 3-phenyl-2-(3,4,5-trimethoxybenzylsulfinyl)-4(3H)-quinazolinone, 3-phenyl-2-(4-pyridylmethylsulfinyl)-4(3H)-quinazolinone, 5-methyl-3-phenyl-2-(2-pyridylmethylsulfinyl)-4(3H)-quinazolinone, 7-chloro-3-phenyl-2-(2-pyridylmethylsulfinyl)-4(3H)-quinazolinone, 3-(1-naphthyl)-2-(2-pyridylmethylsulfinyl)-4(3H)-quinazolinone, 3-isobutyl-2-(2-pyridylmethylsulfinyl)-4(3H)-quinazolinone, 3-phenyl-2-(2-quinolylmethylsulfinyl)-4(3H)-quinazolinone, 3-phenethyl-2-(2-pyridylmethylsulfinyl)-4(3H)-quinazolinone, 2-(2-furylmethylsulfinyl)-3-phenyl-4(3H)-quinazolinone, 3-phenyl-2-(2-thienylmethylsulfinyl)-4(3H)-quinazolinone, 2-(o-dimethylaminobenzylsulfinyl)-3-phenyl-4(3H)-quinazolinone, 6-bromo-3-phenyl-2-(2-pyridylmethylsulfinyl)-4(3H)-quinazolinone, 8-methyl-3-phenyl-2-(2-pyridylmethylsulfinyl)-4(3H)-quinazolinone, 6-chloro-3-phenyl-2-(2-pyridylmethylsulfinyl)-4(3H)-quinazolinone, 6-methyl-3-phenyl-2-(2-pyridylmethylsulfinyl)-4(3H)-quinazolinone, 2-[(4-methylpyridine-2-yl)methylsulfinyl]-3-phenyl-4(3H)-quinazolinone, 2-[(4-methoxy-5-methylpyridine-2-yl)methylsulfinyl]-3-phenyl-4(3H)-quinazolinone, 3-(2-chlorophenyl)-2-(2-pyridylmethylsulfinyl)-4(3H)-quinazolinone, 3-(4-methoxyphenyl)-2-(2-pyridylmethylsulfinyl)-4(3H)-quinazolinone, 3-(3-methoxyphenyl)-2-(2-pyridylmethylsulfinyl)-4(3H)-quinazolnnone, 2-[(4-methoxy-5-methylpyridine-2-yl)methylsulfinyl]-6-methyl-3-phenyl-4(3H)-quinazolinone, 3-(4-methylphenyl)-2-(2-pyridylmethylsulfinyl)-4(3H)-quinazolinone, 2-[(4-methoxy-3-methylpyridine-2-yl)methylsulfinyl]-3-(4-methoxyphenyl)-6-methyl-4(3H)-quinazolinone, 3-phenyl-2-(3-pyridylmethysulfinyl)-4(3H)-quinazolinone, 3-phenyl-2-(4-quinolymethylsufinyl)-4(3H)-quinazolinone, 3-(4-methylphenyl)-2-(4-pyridylmethylsulfinyl)-4(3H)-quinazolinone and 8-methyl-3-phenyl-2-(4-pyridylmethylsulfinyl)-4(3H)-quinazolinone.

The compounds of formula (I) according to the invention can be prepared by subjecting to an oxidation reaction the 4(3H)-quinazolinone derivatives of formula (II)

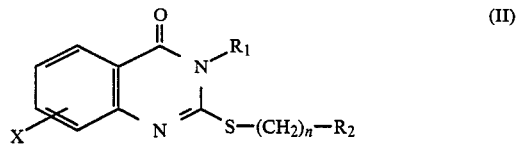

wherein $R_1$, $R_2$, n and X have the same meanings as defined above.

The oxidizing agents used in the oxidation reaction include peroxides e.g. peracetic acid, perbenzoic acid, m-chloro-perbenzoic acid or hydrogen peroxide; halogen atoms e.g. bromine; N-bromosuccinimide, nitric acid, chromic acid, potassium permanganate, sodium metaperiodate and the like.

The oxidizing reaction is generally carried out by using the oxidizing agent in an equal or excess amount to the compound of formula (II). This reaction can be conducted in an aqueous medium, but preferably in an organic solvent e.g. a halogenated hydrocarbon such as carbon tetrachloride, dichloromethane, dichloroethane, chloroform and the like or acetic acid. The reaction conditions such as reaction temperature, reaction time and the like are different depending on the kinds of the solvents, starting materials and oxidizing agents used in the reaction. For example, the reaction can be carried out at temperatures in the range between $-40°$ C. and $10°$ C., preferably between $-20°$ C. and $30°$ C. for the times between several minutes and several hours, in the case where m-chloroperbenzoic acid is used as the oxidizing agent and chloroform is used as the reaction solvent.

The starting compounds of formula (II) are prepared by reacting the compounds of formula (III)

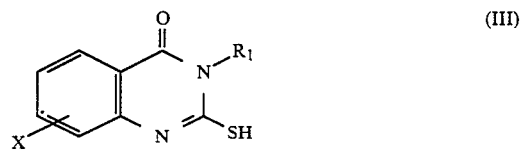

wherein $R_1$ and X have the meanings as defined above with the compounds of formula (IV)

$$R_2-(CH_2)_n-Y \qquad (IV)$$

wherein $R_2$ has the meaning as defined above and Y is a halogen atom such as chlorine, bromine and iodine in the presence of a base e.g. inorganic bases, alkali metal alkoxides and the like.

The reaction can be performed using 0.5 to 5 moles of the compounds of formula (IV) per mole of the compounds of formula (III), in water and/or organic solvents such as lower alcohols, polar solvents, etheric solvents, ethyl, acetate, acetone and the like, and at temperatures between $0°$ C. and $150°$ C.

Some of the 4(3H)-quinazolinone derivatives represented by formula (III) are disclosed in J. Chem. Soc., vol. 82, p 964(1960); J. Med. Chem. 1983, 26, 218–222; Chem. Abstr., vol 83 131542q(1975) and Chem. Abstr., vol. 92 146713f(1980).

The compounds of formula (I) may be converted, if desired, to pharmaceutically acceptable acid addition salts thereof and these salts are included within the scope of this invention.

Concrete examples of addition salts include the salts of the compounds with inorganic acids such as hydrochloric acid, hydrobromic acid, hydroiodic acid, nitric acid, sulfuric acid or phosphoric acid and organic acids such as formic acid, acetic acid, propionic acid, butyric acid, maleic acid, malonic acid, malic acid, citric acid, tartaric acid or oxalic acid.

The compounds of formula (I) and pharmaceutically acceptable acid addition salts thereof are of prominent antiulcer activity.

Thus, the present invention also relates to pharmaceutical compositions which comprise as an active ingredient the compounds of formula (I) or pharmaceutically acceptable acid addition salts thereof.

The pharmaceutical compositions of the invention may be formulated into various forms which are commonly used in the art and which are administered orally or parenterally. For example, they may be formulated into tablets, capsules, suppositories, troches, syrups, creams, ointments, granules, powders, injectable solutions or suspensions. Alternatively, they may be formulated into double or multiple layer tablets, together with other active principles. Furthermore, they may be formulated into coated tablets such as sugar-coated tablets, enteric-coated tablets and film-coated tablets.

In order to obtain solid preparations, the compounds of this invention are mixed with such conventional diluents or fillers as lactose, refined sugar, crystalline cellulose, corn starch, calcium phosphate, sorbitol, glycine, carboxymethylcellulose, gum arabic, polyvinylpyrrolidone, hydroxypropylcellulose, glycerol, polyethylene glycol, stearic acid, megnesium stearate or talc.

In order to obtain semi-solid preparations, the compounds of this invention are mixed with such additives as plant wax, synthetic wax or fats.

In order to obtain liquid preparations, the compounds of this invention are mixed with such diluents or additives as sodium chloride, sorbitol, glycerol, olive oil, almond oil, propylene glycol or ethanol.

The compounds of the invention may normally be contained in a preparation in an amount of from 0.1 to 100% by weight, more suitably in an amount of from 1 to 50% by weight in the case of preparations for oral administration and from 0.2 to 20% by weight in the case of injectable preparations.

There is no particular limitation as to the method of administration and the dosage of the autiulcer agents according to the invention. They are chosen, depending on the form of preparation, age of patients, sex, degree of symptom, etc. Normally, however, the dosage will be in the range of from 10 to 1,000 mg per day.

The pharmaceutical composition of the invention may be administered in conjunciton with one or more other active principles such as antiacids, non-steroid antiinflammatory agents or other types of antiulcer agents.

BEST MODE OF CARRYING OUT THE INVENTION

The invention will be explained in more detail by the following Examples, which are to be understood not to limit the scope of this invention.

PREPARATION OF THE STARTING COMPOUNDS OF FORMULA (II)

Preparative Example 1

3-Phenyl-2-(2-pyridylmethylthio)-4-(3H)-quinazolinone 6.1 ml of 28% methanolic solution of sodium methoxide and 2.46 g of 2-chloromethylyridine hydrochloride were added to a solution of 3.62 g of 2-mercapto-3-phenyl-4(3H)-quinazolinone in 100 ml of methanol, and the stirring was continued at room temperature for 2.5 hours. About 50 ml of water were added to the reaction solution and crystals precipitated were collected by filtration and recrystallized from ethyl acetate to give 2.45 g of the title compound.

White crystals
M.P. 182.3–183.3° C.
NMR(CDCl$_3$, δ): 4.56(2H,s), 7.10–7.79(11H,m), 8.25(1H,d), 8.52(1H,d)
IR(nujol,cm$^{-1}$): 1680, 1610. 1590

Preparative Example 2

3-Ethyl-2-(2-pyridylmethylthio)-4(3H)-quinazolinone 7.0 ml of 28% methanolic solution of sodium methoxide and 2.82 g of 2-chloromethylpyridine hydrochloride were added, in turn, to a solution of 3.56 g of 3-ethyl-2mercapto-4(3H)-quinazolinone in 50 ml of methanol, and the stirring was continued at room temperature for 4 hours. The reaction solution was poured into about 300 ml of water and extracted with chloroform. The extract was dried over sodium sulfate and the solvent was distilled off under reduced pressure. The residue was recrystallized from a mixture of ethyl acetate and diisopropyl ether, to give 2.47 g of the title compound.

White crystals
M.P. 110.1–111.1° C.
NMR(CDCl$_3$,δ): 1.36(3H,t), 4.26(2H,q), 4.67(2H,s), 7.14–7.74(6H,m), 8.21(1H,d), 8.59(1H,d)
IR(nujol,cm$^{-1}$): 1675, 1610, 1550

Preparative Example 3

3-Isobutyl2-(2-pyridylmethylthio)-4-(3H)-quinazolinone 5.4 ml of 28% methanolic solution of sodium methoxide and 2.3 g of 2-chloromethylpyridine hydrochloride were added, in turn, to a solution of 3.0 g 3-isobutyl-2-mercapto-4(3H-)quinazolinone in 50 ml of methanol, and the stirring was continued at room temperature for 15 hours. The reaction solution was poured into about 300 ml of water and extracted with chloroform. The extract was dried over sodium sulfate and the solvent was distilled off under reduced pressure. The residue was purified by silica column chromatography eluted with 10% ethyl acetate in chloroform. The fraction obtained from the eluent was further purified by crystallization from a mixture of ethyl acetate and diisopropylether to give 1.92 g of the title compound.

White crystals
M.P. 91.7–93.2° C.
NMR(CDCl$_3$,δ): 0.96(6H,d), 2.22–2.41(1H,m), 4.02(2H,d), 4.68(2H,s), 7.13–7.76(6H,m), 8.22(1H,d), 8.59(1H,d)
IR(nujol,cm$^{-1}$): 1665, 1610, 1595, 1540

Preparative Example 4

6-Methyl-3-phenyl-2-(2-pyridylmethylthio)-4(3H)-quinazolinone 9.5 ml of 28% methanolic solution of sodium methoxide were added to a solution of 6.0 g of 2-mercapto-6-methyl-3-phenyl-4(3H)-quinazolinone and 4.0 g of 2-chylormethylpyridine hydrochloride in methanol, the mixture was stirred at room temperature for 2 hours and allowed to stand overnight. Crystals precipitated were collected by filtration and recrystallized from ethyl acetate to give 4.2 g (52.2%) of the title compound.

White crystals
M.P. 167.2–169.2° C. NMR(CDCl$_3$,δ): 2.48(3H,s), 4.55(2H,s), 7.10–7.20(1H,m), 7.25–7.36(2H,m), 7.45–7.69(7H,m), 8.02(1H,s), 8.53(1H,d)
IR(nujol,cm$^{-1}$): 1685

Preparative Example 5

3-Phenyl-2-[(4-methylpyridin-2-yl)methylthio]-4(3H)-quinazolinone 8.7 ml of 28% methanolic solution of sodium methoxide were added to a solution of 5.0 g of 2-mercapto-3-phenyl-4(3H)-quinazolinone and 4.0 g of 2-chloromethyl-4-methylpyridine hydrochloride in methanol, and the stirring was continued at room temperature for 5 hours. The reaction solution was poured into water and extracted with chloroform. The chloroform layer was washed with an aqueous solution of sodium carbonate and dried over sodium sulfate. The solvent was distilled off under reduced pressure and the residue was purified by silica gel column chromatography. The fraction eluted with 8% ethyl acetate in chloroform was collected and crystallized from ethyl acetate to give 2.17 g (30.7%) of the title compound.

White crystals
M.P. 144.6–150.1° C.
NMR(CDCl$_3$,67 ): 2.32(3H,s), 4.53(2H,s), 6.98(1H,d), 7.26–7.80(9H,m), 8.25(1H,d), 8.38(1H,d)
IR(nujol,cm$^{-1}$) 1695, 1660

EXAMPLE 1

3-Phenyl-2-(2-pyridylmethylsulfinyl)-4(3H)-quinazolinone 0.98 g Of m-chloroperbenzoic acid was added under an ice-cold water cooling to 1.8 g of a solution of 3-phenyl-2-(2-pyridylmethylthio)-4(3H)-quinazolinone in 50 ml of chloroform and the stirring was continued for 1.5 hours.

The reaction solution was washed with an aqueous solution of sodium carbonate, dried over sodium sulfate and distilled off under reduced pressure. Crystallization of the residue from ethyl acetate gave 1.26 g (66.8% yield) of the title compound as white crystals.

M.P 147.4–148.7° C.
NMR(CDCl$_3$,67 ): 4.25(1H,d,J=12Hz), 4.48(1H,d,J=12Hz), 7.06–7.85(11H,m), 8.22–8.35(2H,m)
IR(nujol,cm$^{-1}$) 1685, 1600, 1580, 1560, 1060

EXAMPLE 2

The following compounds (a) to (c) were prepared from the corresponding sulfides by a similar way to that mentioned in Example 1.

(a) 3-ethyl-2-(2-pyridylmethylsulfinyl)-4(3H)-quinazolinone
Yield 25.9%
White crystals (from ethyl acetate)
M.P. 115.3–116.3° C., (dec)
NMR(CDCl$_3$,δ): 1.37(3H,t), 3.93–4.10(1H,m), 4.28–4.46(1H,m), 4.65(1H,d,J=12Hz), 4.85(1H,d,J=12Hz), 7.18–7.89(6H,m), 8.30(1H,d), 8.48(1H,d)
IR(nujol,cm$^{-1}$): 1660, 1590, 1560, 1070

(b) 2-(benzylsulfinyl)-3-phenyl-4(3H)-quinazolinone
Yield 71.3%
White crystals (from benzene)
M.P. 192.2–193.3° C.
NMR(CDCl$_3$,δ): 4.18(1H,d,J=12Hz), 4.51(1H,d,J=12Hz), 6.50(1H,d), 6.95–7.71(10H,m), 7.85–8.08(2H,m), 8.34(1H,d)
IR(nujol,cm$^{-1}$): 1690, 1600, 1585, 1565, 1070

(c) 3-phenyl-2-(3,4,5-trimethoxybenzylsulfinyl)-4(3H)-quinazolinone
Yield 55.7%
White crystals (from ethyl acetate)
M.P. 130.1–134.9° C.
NMR(CDCl$_3$,δ): 3.63(6H,s), 3.80(3H,s), 4.09(1H,d,J=12Hz), 4.36(1H,d,J=12Hz), 6.16(2H,s), 6.75(1H,d), 7.36–7.69(5H,m), 7.90(1H,t), 8.05 (1H,d), 8.34 (1H,d),
IR(nujo,cm$^{-1}$) 1700, 1590, 1560, 1070

EXAMPLE 3

3-Phenyl-2-(4-pyridylmethylsulfinyl)-4(3H)-quinazolinone 0.7 g Of m-chloroperbenzoic acid was added under an ice-cold water cooling to 1.12 g of a solution of 3-phenyl-2(4-pyridylmethylthio)-4(3H)-quinazolinone in 50 ml of chloroform and the stirring was continued for 2 hours.

The reaction solution was washed with an aqueous solution of sodium carbonate, dried over sodium sulfate, distilled off under reduced pressure and the residue was purified by silica chromatography.

The fraction eluted with acetone-chloroform (1:1) was crystallized from ethyl acetate to give 0.40 g (3.41% yield) as white crystals.

M.P. 148.6–149.7° C. (dec)
NMR(CDCl$_3$,δ): 4.10(1H,d,J=12Hz), 4.34(1H,d,J=12Hz), 6.94–7.06(3H,m), 7.38–8.03(7H,m), 8.36(1H,d), 8.52(2H,m)
IR(nujol,cm$^{-1}$) 1695, 1605, 1590, 1570, 1075

EXAMPLE 4

The following compounds (a) to (i) were prepared from the corresponding sulfides by a similar way to that mentioned in Example 3.

(a) 5-methyl-3-phenyl-2-(2-pyridylmethylsulfinyl)-4(3H)-quinazolinone
Yield 49.5%
White crystals (from ethyl acetate)
M.P. 154.6–155.6° C. (dec)
NMR(CDCl$_3$,δ): 4.28(1H,d,J=12Hz), 4.53(1H,d,J=12Hz), 7.09–7.69(11H,m), 8.32(1H,d)
IR(nujol,cm$^{-1}$) 1700, 1610, 1580, 1560, 1070

(b) 7-chloro-3-phenyl-2-(2-pyridylmethylsulfinyl)-4(3H)-quinazolinone
Yield 29.7%
White needles (from ethyl acetate)
M.P. 157.1–157.9° C. (dec)
NMR(CDCl$_3$,δ): 4.23(1H,d,J=12Hz), 4.48(1H,d,J=12Hz), 7.08–7.79(10H,m), 8.20–8.29(2H,m)
IR(nujol,cm$^{-1}$): 1700, 1600, 1580, 1560, 1060

(c) 3-(1-naphthyl)-2-(2-pyridylmethylsulfinyl)-4(3H)-quinazolinone

The resultant title compound forms the diastereoisomers of rotational isomerism by the naphthyl group at the 3position and optional isomerism by the sulfinyl group at the 2position. The respective diastereoisomers were separated by silica chromatography. The initially effusing fraction was identified as I, and the subsequently effusing fraction was identified as II.

I. Yield 19.9%
White crystals (from ethyl acetate)
M.P. 176.8–178.7° C. (dec)
NMR(CDCl$_3$,δ): 4.12(1H,d,J=12Hz), 4.46(1H,d,J=12Hz), 7.03–7.14(2H,m), 7.44–7,72(7H,m), 7.85–8.22(5H,m), 8.37(1H,d)
IR(nujol,cm$^{-1}$): 1690, 1590, 1560, 1045
MASS: 411(M+), 363, 288, 271(100%), 217

II. Yield 3.9%
White crystals (from ethyl acetate)
M.P. 164.9–167.8° C. (dec)
NMR(CDCl$_3$,δ): 4.35(1H,d,J=12Hz), 4.50(1H,d,J=12Hz), 7.10–7.70(9H,m), 7.82–8.14(5H,m), 8.29–8.40(2H,m)
IR(nujol,cm$^{-1}$): 1700, 1590, 1560, 1070
MASS: 411(M+), 363, 288, 271(100%), 217

(d) 3-isobutyl-2-(2-pyridylmethylsulfinyl)-4(3H)-quinazolinone
Yield 48.5%
White crystals (from ethyl acetate/isopropyl ether)
M.P. 103.1–106.1° C.
NMR(CDCl$_3$,δ): 0.89–1.02(6H,dd), 2.05–2.30(1H,m), 3.66–3.82(1H,dd), 4.15–4.29(1H,dd), 4.67(1H,d,J=13Hz), 4.88(1H,d,J=13Hz), 7.04–7.91(6H,m), 8.30(1H,d), 8.46(1H,d)
IR(nujol,cm$^-$): 1685, 1600, 1590, 1560, 1055

(e) 3-phenyl-2-(2-quinolylmethylsulfinyl)-4(3H)-quinazolinone
Yield 53.7%
Pale yellow crystals (from ethyl acetate)
M.P. 153.7–157.0° C. (dec)

NMR(CDCl$_3$,δ): 4.39(1H,d,J=12Hz), 4.68(1H,d,J=12Hz), 7.28-7.83(13H,m), 8.06(1H,d), 8.28(1H,d)

IR(nujol): 1705, 1605, 1590, 1570, 1085

(f) 3-phenethyl-2-(2-pyridylmethylsulfinyl)-4(3H)-quinazolinone

Yield 46.9%

Transparent, yellow oily product

NMR(CDCl$_3$,δ): 2.92-3.10(2H,m), 4.05-4.29(1H,m), 4.41-4.68(2H,m), 4.78(1H,d,J=12Hz), 7.06-7.89(13H,m), 8.30(1H,d), 8.42(1H,d)

IR(neat, cm$^{-1}$) 1690, 1590, 1565, 1070

(g) 2-(2-furylmethylsulfinyl)-3-phenyl-4(3H)-quinazolinone

Yield 44.5%

White crystals (from ethyl acetate)

M.P. 131.2-132.6° C.(dec)

NMR(CDCl$_3$,δ): 4.21(1H,d,J=12Hz), 4.50(1H,d,J=12Hz), 6.24-6.33(2H,m), 6.89(1H,d), 7.21-7.68(6H,m), 7.81-8.00(2H,m), 8.35(1H,d)

IR(nujol,cm$^{-1}$): 1700, 1605, 1585, 1565, 1050

(h) 3-phenyl-2-(2-thienylmethylsulfinyl)-4(3H)-quinazolinone

Yield 45.3%

White crystals (from ethyl acetate)

M.P. 143.3-144.0° C.(dec)

NMR(CDCl$_3$,δ): 4.39(1H,d,J=12Hz), 4.82(1H,d,J=12Hz), 6.61(1H,d), 6.82-7.00(2H,m), 7.20-7.72(6H,m), 7.90(1H,t), 8.02(1H,d), 8.35(1H,d)

IR(nujol,cm$^{-1}$): 1685, 1600, 1590, 1565, 1070

(i) 2-(o-dimethylaminobenzylsulfinyl)-3-phenyl-4(3H)-quinazolinone

Yield 8%

White crystals (from ethyl acetate)

M.P. 136.8-139.8° C.(dec)

NMR(CDCl$_3$,δ): 2.38(6H,s), 4.42(1H,d,J=12Hz), 4.67(1H,d,J=12Hz), 6.29(1H,d), 6.95-7.68(9H,m), 7.89(1H,t), 8.03(1H,d), 8.33(1H,d)

IR(nujol,cm$^{-1}$): 1685, 1605, 1585, 1560, 1070

EXAMPLE 5

6-Bromo-3-phenyl-2-(2-pyridylmethylsulfinyl)-4(3H)-quinazolinone 2.4 g Of m-chloroperbenzoic acid was added under an ice-cold water cooling to 4.9 g of a solution of 6-bromo-3-phenyl-2-(2-pridylmethylthio)-4(3H)-quinazolinone chloroform and the stirring was continued for 2.5 hours. The reaction solution was washed with an aqueous solution of sodium carbonate, dried over sodium sulfate, distilled-off under reduced pressure and the residue was purified by silica gel column chromatography. The fraction eluted with 20% ethyl acetate/chloroform was crystallized from acetone to give 1.54 g (30.2% yield) of the title compound as white crystals.

White crystals

M.P. 190.6-191.8° C. (dec)

NMR(CDCl$_3$,δ): 4.20(1H,d,J=13Hz), 4.43(1H,d,J=13Hz), 7.06-7.16(1H,m), 7.22-7.30(1H,m), 7.36-7.69(7H,m), 7.88(1H,dd), 8.24(1H,d), 8.44(1H,d)

IR(nujol,cm$^{-1}$) 1690, 1070

EXAMPLE 6

The following compounds (a) to (o) were prepared from the corresponding sulfides by a similar way to that mentioned in Example 5.

(a) 8-methyl-3-phenyl-2-(2-pyridylmethylsulfinyl)-4(3H)-quinazolinone

Yield 48.6%

White crystals (from ethyl acetate/isopropyl ether)

M.P. 154.7-156.1° C. (dec)

NMR(CDCl$_3$,δ): 2.61(3H,s), 4.40(1H,d,J=13Hz), 4.74(1H,d,J=13Hz), 7.09-7.18(1H,m), 7.21-7.31(2H,m), 7.40-7.76(7H,m), 8.17(1H,d), 8.32(1H,d)

IR(nujol,cm$^{-1}$) 1695, 1610, 1060

(b) 6-chloro-3-phenyl-2-(2-pyridylmethylsulfinyl)-4(3H)-quinazolinone

Yield 33.7%

White crystals (from chloroform/isopropyl ether)

M.P. 193.7-194.3° C. (dec)

NMR(CDCl$_3$,δ): 4.21(1H,d,J=13Hz), 4.44(1H,d,J=13Hz), 7.08-7.17(1H,m), 7.23-7.32(1H,m), 7.35-7.47(2H,m), 7.51-7.76(6H,m), 8.22-8.31(2H,m)

IR(nujol,cm$^{-1}$): 1690, 1600, 1065

(c) 6-methyl-3-phenyl-2-(2-pyridylmethylsulfinyl)-4(3H)-quinazolinone

Yield 52.0%

White crystals (from ethyl acetate)

M.P. 168.8-170.0° C. (dec)

NMR(CDCl$_3$,δ): 2.52(3H,s), 4.25(1H,d,J=13Hz), 4.48(1H,d,J=13Hz), 7.08-7.16(1H,m), 7.21-7.75(9H,m), 8.10(1H,s), 8.28(1H,d)

IR(nujol,cm$^{-1}$): 1680, 1620, 1060

(d) 2-[(4-methylpyridin-2-yl)methylsulfinyl]-3-phenyl-4(3H)-quinazolinone

Yield 37.8%

White crystals (from ethyl acetate/isopropyl ether)

M.P. 149.2-151.2° C. (dec)

NMR(CDCl$_3$,δ): 2.29(3H,s), 4.23(1H,d,J=13Hz), 4.45(1H,d,J=13Hz), 6.93(1H,d), 7.09(1H,s), 7.30-7.70(6H,m), 7.78-7.87(2H,m), 8.12(1H,d), 8.34(1H,d)

IR(nujol,cm$^{-1}$): 1690, 1600, 1060

(e) 2-[(4-methoxy-5-methylpyridin-2-yl)methylsulfinyl]-3-phenyl-4(3H)-quinazolinone Yield 17.1%

White crystals (from ethyl acetate/isopropyl ether)

M.P. 148.7-150.8° C. (dec)

NMR(CDCl$_3$,δ): 2.05(3H,s), 3.78(3H,s), 4.26(1H,d,J=13Hz), 4.46(1H,d,J=13Hz), 6.69(1H,s), 7.21-7.68(6H,m), 7.79-7.94(3H,m), 8.34(1H,d)

IR(nujol,cm$^{-1}$): 1700, 1600, 1075

(f) 3-(2-chlorophenyl)-2-(2-pyridylmethylsulfinyl)-4(3H)-quinazolinone

Yield 29.9%

White crystals (from ethyl acetate/isopropyl ether)

M.P. 146.8-148.5° C. (dec)

NMR(CDCl$_3$,δ): 4.58(1H,d,J=13Hz), 4.77(1H,d,J=13Hz), 7.13-7.22(1H,m), 7.31(1H,d), 7.48-7.71(6H,m), 7.84-8.00(2H,m), 8.37(1H,d), 8.50(1H,d)

IR(nujol,cm$^{-1}$): 1710, 1600, 1080

(g) 3-(4-methoxyphenyl)-2-(2-pyridylmethylsulfinyl)-4(3H)-quinazolinone

Yield 30.3%

White crystals (from ethyl acetate/isopropyl ether)

M.P. 153.9° C. (dec)

NMR(CDCl$_3$,δ): 3.89(3H,s), 4.27(1H,d,J=13Hz), 4.46(1H,d,J=13Hz), 7.00-7.15(3H,m), 7.24-7.39(3H,m), 7.50-7.85(4H,m), 8.20-8.35(2H,m)

IR(nujol,cm$^{-1}$): 1700, 1620, 1080

(h) 3-(3-methoxyphenyl)-2-(2-pyridylmethylsulfinyl)-4(3H)-quinazolinone
Yield 40.6%
White crystals (from ethyl acetate/isopropyl ether)
M.P. 14.5–148.7° C. (dec)
NMR(CDCl$_3$,δ): 3.84(3H,s), 3.86(3H,s), 4.35(1H,d,J=13Hz), 4.53(1H,dd,J=13Hz,6Hz), 6.88–7.35(5H,m), 7.40–7.86(5H,m), 8.22–8.37(2H,m)
IR(nujol,cm$^{-1}$): 1695, 1610, 1070

(i) 2-[(4-methoxy-5-methylpyridin-2-yl)methylsulfinyl-6-methyl-3-phenyl-4(3H)-quinazolinone
Yield 27.6%
White crystals (from ethyl acetate/isopropyl ether)
M.P. 155.8° C. (dec)
NMR(CDCl$_3$,δ): 2.06(3H,s), 2.54(3H,s), 3.79(3H,s), 4.31(1H,d,J=13Hz), 4.48(1H,dd,J=13Hz), 6.71(1H,s), 7.22–7.79(7H,m), 7.94(1H,s), 8.12(1H,s)
IR(nujol,cm$^{-1}$): 1685, 1600, 1075

(j) 3-(4-methylphenyl)-2(2-pyridylmethylsulfinyl)-4(3H)-quinazolinone
Yield 55.5%
White crystals (from ethyl acetate/isopropyl ether)
M.P. 147.8° C. (dec)
NMR(CDCl$_3$,δ): 2.46(3H,s), 4.28(1H,d,J=13Hz), 4.48(1H,d,J=13Hz), 7.07–7.16(1H,m), 7.20–7.88(9H,m), 8.24–8.37(2H,m)
IR(nujol,cm$^{-1}$): 1685, 1070

(k) 2-[(4-methoxy-3-methylpyridin-2-yl)methylsulfinyl]-3-(4-methoxyphenyl)-6-methyl-4(3H)-quinazolinone
Yield 34.1%
White crystals (from ethyl acetate/isopropyl ether)
M.P. 161.5° C. (dec)
NMR(CDCl$_3$,δ): 2.16(3H,s), 2.50(3H,s), 3.82(3H,s), 3.88(3H,s), 4.41(1H,d,J=14Hz), 5.01(1H,d,J=14Hz), 6.61(1H,d), 6.95–7.25(3H,m), 7.39(1H,d), 7.60(1H,d), 7.72(1H,d), 8.02(1H,d), 8.09(1H,s)
IR(nujol,cm$^{-1}$): 1675, 1610, 1050

(l) 3-phenyl-2-(3-pyridylmethylsulfinyl)-4(3H)-quinazolinone
Yield 47.9%
White crystals (from ethyl acetate)
M.P. 101.3–102.7° C. (dec)
NMR(CDCl$_3$,δ): 4.13(1H,d,J=13Hz), 4.37(1H,d,J=13Hz), 6.91–7.01(1H,m), 7.19–7.28(1H,m), 7.33–7.70(6H,m), 7.82–8.01(2H,m), 8.22(1H,s), 8.34(1H,d), 8.56(1H,d)
IR(nujol,cm$^{-1}$): 1690, 1600, 1070

(m) 3-phenyl-2-(4-quinolylmethylsulfinyl)-4(3H)-quinazolinone
Yield 27.3%
White crystals (from ethyl acetate)
M.P. 150° C. (dec)
NMR(CDCl$_3$,δ): 4.53(1H,d,J=12Hz), 4.85(1H,d,J=12Hz), 6.78(1H,d), 7.16–7.80(9H,m), 7.91(1H,t), 8.01–8.17(2H,m), 8.33(1H,d), 8.79(1H,d)
IR(nujol,cm$^{-1}$): 1690, 1600, 1090

(n) 3-(4-methylphenyl)-2-(4-pyridylmethylsulfinyl)-4(3H)-quinazolinone
Yield 48.0%
White crystals (from ethyl acetate)
M.P.160.1–162.0° C.
NMR(CDCl$_3$,δ): 2.49(3H,s), 4.15(1H,d,J=12Hz), 4.34(1H,d,J=12Hz), 6.95(1H,d), 7.06–7.14(2H,m), 7.25–7.46(3H,m), 7.64(1H,t), 7.82–7.99(2H,m), 8.34(1H,d), 8.54(2H,d)
IR(nujol,cm$^{-1}$): 1695, 1600, 1075

(o) 8-methyl-3-Phenyl-2-(4-pyridylmethylsulfinyl)-4(3H)-quinazolinone
Yield 44.2%
White crystals (from ethyl acetate)
M.P. 164.2–166.1° C.
NMR(CDCl$_3$,δ): 2.74(3H,s), 4.22(1H,d,J=13Hz), 4.49(1H,d,J=13Hz), 6.90(1H,d), 7.05(2H,d), 7.36–7.64(5H,m), 7.73(1H,d), 8.17(1H,d), 8.52(2H,d)
IR(nujol,cm$^{-1}$): 1695, 1600, 1050

EXAMPLE 7

The antiulcer activity of the compounds of this invention was determined by the following method.

Four-week-old ddY series male mice were used as the test animals after they were fasted for 24 hours. Each test compound suspended in a 1% gum arabic solution was administerd to the stomach of each mouse at a dose of 100 mg/kg, and then, after 30 minutes, 20 mg/kg of indomethacin was administered orally. Four hours after the administration of indomethacin, the stomach of mouse was extirpated and the length of ulcers was measured. Then, the ulcer index was determined by the total sum of the scores as calculated in Table 1.

TABLE 1

| Length of ulcer | 0.5 mm< | 1 mm< | 2 mm< | 3 mm< |
|---|---|---|---|---|
| Score | 0.5 | 1 | 2 | 3 |

The mean ulcer index of each group was calculated and the suppression rate against the control group in terms of difference in the mean ulcer index was determined. The results are shown in Table 2.

TABLE 2

| Compound tested | Suppression rate of indomethacin induced ulcer, 100 mg/kg, p.o. |
|---|---|
| 3-phenyl-2-(2-pyridylmethylsulfinyl)-4(3H)—quinazolinone | 83 |
| 3-phenyl-2-(4-pyridylmethylsulfinyl)-4(3H)—quinazolinone | 69 |
| 5-methyl-3-phenyl-2-(2-pyridylmethylsulfinyl)-4(3H)—quinazolinone | 77 |
| 3-(1-naphthyl)-2-(2-pyridylmethylsulfinyl)-4(3H)—quinazolinone | 39 |
| 3-isobutyl-2-(2-pyridylmethylsulfinyl)-4(3H)—quinazolinone | 40 |
| 6-methyl-3-phenyl-2-(2-pyridylmethylsulfinyl)-4(3H)—quinazolinone | 56 |
| 2-[(4-methylpyridin-2-yl)methylsulfinyl]-3-phenyl-4(3H)—quinazolinone | 68 |
| 2-[(4-methoxy-5-methylpyridin-2-yl)methylsulfinyl]-3-phenyl-4(3H)—quinazolinone | 82 |
| 3-(2-chlorophenyl)-2-(2-pyridylmethylsulfinyl)-4(3H)—quinazolinone | 56 |
| 3-(4-methoxyphenyl)-2-(2-pyridylmethylsulfinyl)-4(3H)—quinazolinone | 72 |
| 3-(3-methoxyphenyl)-2-(2-pyridylmethylsulfinyl)-4(3H)—quinazolinone | 73 |
| 2-[(4-methoxy-5-methylpyridin-2-yl)methylsulfinyl]-6-methyl-3-phenyl-4(3H)—quinazolinone | 59 |
| 3-(4-methylphenyl)-2-(2-pyridylmethylsulfinyl)-4(3H)—quinazolinone | 73 |
| 2-[(4-methoxy-3-methylpyridin-2-yl)methylsulfinyl]-3-(4-methoxyphenyl)-6-methyl-4(3H)—quinazolinone | 51 |
| 3-phenyl-2-(3-pyridylmethylsulfinyl)-4(3H)—quinazolinone | 55 |
| 3-phenyl-2-(4-quinolylmethylsulfinyl)-4(3H)—quinazolinone | 64 |
| Cimetidine(control) | 40 |

As shown in Table 2, it is evident that the compounds of the invention possess the antiulcer activity comparable to or superior to that of cimetidine.

The compounds of this invention have generally low toxicity.

For example, $LD_{50}$ value(P.O) of 3-phenyl-2-(2-pyridylmethylsulfinyl)-4(3H)-quinazolinone is higher thn 3,000 mg/kg. The reversion test on the compound reveals the negative result.

Examples in which the compounds of present invention are formulated into various preparations are illustrated below.

Preparation 1. Tablet 50 mg Of 3-phenyl-2-(2-pyridylmethylsulfinyl)-4(3H)-quinazolinone, 77 mg of lactose, 15 mg of crystalline cellulose, 7 mg of corn starch and 1 mg of magnesimm stearate (each per tablet) were thoroughly mixed, and then the mixture was tableted with a rotary tableting machine into a tablet of 7mm diameter, weight 150 mg.

Preparation 2. Granule 50 mg Of 3-phenyl-2-(2-pyridylmethylsulfinyl)-4(3H)-quinazolonone 230 mg of lactose, 110 mg of corn starch and 100 mg of crystalline cellulose were thoroughly mixed. Meanwhile, 10 mg of hydroxypropylcellulose were dissolved in 90 mg of ethanol and the solution was added to the previously prepared mixture. The whole mixture was kneaded and granulated. The granules were air-dried at 50° C. and then sieved into the grain size of from 297 μm to 1460 μm. 500 mg Of the granules were packed into a unit dosage form.

Preparation 3. Syrup 5 g Of 3-phenyl-2-(2-pyridylmethylsulfinyl)-4(3H)-quinazolinone, 30 g of refined sugar, 25 g of 70 w/v % D-sorbitol, 0.03 g of ethyl p-hydroxybenzoate and 0.015 g of propyl p-hydroxybenzoate were dissolved in 60 ml of warmed water. After the solution was cooled, a solution of 0.2 of a flavor in 0.15 g of glycerol and 0.5 g of 96% ethanol was added. The whole mixture was diluted with water to balance 100 ml.

Preparation 4. Injectable solution 5 mg Of 3-phenyl-2-(2-pyridylmethylsulfinyl)-4(3H)-quinazolinone and 10 mg of sodium chloride were dissolved in sterilized distilled water to balance 1 ml.

Preparation 5. Suppository 20 g Of polyethylene glycol 4000 were added to a solution of 10 g of 3-phenyl-2-(2-pyridylmethylsulfinyl)-4(3H)-quinazolinone in 70 g of glycerol. The mixture was warmed and poured into a suppository mold and then cooled to give suppositories, each weighing 1.5 g.

What is claimed is:

1. A compound of the formula (I)

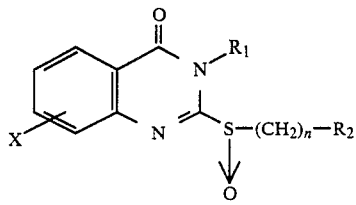

wherein $R_1$ is a $C_1$–$C_6$ alkyl group, phenyl, a $C_1$–$C_6$ alkyl substituted phenyl, a $C_1$–$C_6$ alkoxy-substituted phenyl, a halogen-substituted phenyl, naphthyl, benzyl or phenethyl, $R_2$ is a phenyl group, a $C_1$–$C_6$ alkylamino-substituted phenyl, a $C_1$–$C_6$ alkoxyl-substituted phenyl or a 5- or 6-membered heterocyclic group having one of N, O and S as a hetero atom, said heterocyclic group optionally being substituted by a $C_1$–$C_4$ alkyl or $C_1$–$C_4$ alkoxy, or fused with a benzene ring, n is 1 or 2 and X is hydrogen, a $C_1$–$C_6$ alkyl group or a halogen atom, and pharmaceutically acceptable acid addition salts thereof.

2. A compound of claim 1 wherein $R_1$ is a $C_1$–$C_4$ alkyl group, phenyl, a $C_1$–$C_6$ alkyl-substituted phenyl, a $C_1$–$C_6$ alkoxy-substituted phenyl, a halogen-substituted phenyl, naphthyl, benzyl or phenethyl.

3. A compound of claim 1 wherein $R_2$ is phenyl, a $C_1$–$C_6$ alkylamino-substituted phenyl, a $C_1$–$C_6$ alkoxy-substituted phenyl, furyl, thienyl, pyridyl, quinolyl or a $C_1$–$C_4$ alkyl, and/or $C_1$–$C_4$ alkoxy-substituted pyridyl and n is 1 or 2.

4. A compound of claim 1 wherein X is hydrogen, a $C_1$–$C_4$ alkyl group or a halogen atom.

5. A pharmaceutical composition which comprises as an active ingredient an effective amount of the compound of claim 1 or pharmaceutically acceptable acid addition salts thereof, optionally in admixture with additives for pharmaceutical preparation.

6., A pharmaceutical composition which comprises as an active ingredient an effective amount of the compound of claim 2 or pharmaceutically acceptable acid addition salts thereof, optionally in admixture with additives for pharmaceutical preparation.

7. A pharmaceutical composition which comprises as an active ingredient an effective amount of the compound of claim 3 or pharmaceutically acceptable acid addition salts thereof, optionally in admixture with additives for pharmaceutical preparation.

8. A pharmaceutical composition which comprises as an active ingredient an effective amount of the compound of claim 4 or pharmaceutically acceptable acid addition salts thereof, optionally in admixture with additives for pharmaceutical preparation.

* * * * *